United States Patent [19]

Gsell

[11] Patent Number: 5,063,236
[45] Date of Patent: Nov. 5, 1991

[54] PYRIDYL SUBSTITUTED GUANIDINES USEFUL AS INSECTICIDES

[75] Inventor: Laurenz Gsell, Basle, Switzerland

[73] Assignee: Ciba-Geigy Corporation, Ardsley, N.Y.

[21] Appl. No.: 539,297

[22] Filed: Jun. 18, 1990

Related U.S. Application Data

[63] Continuation of Ser. No. 396,587, Aug. 21, 1989, abandoned, which is a continuation-in-part of Ser. No. 226,357, Jul. 29, 1988, abandoned.

[30] Foreign Application Priority Data

Aug. 4, 1987 [CH] Switzerland ............... 2985/87
Jun. 6, 1988 [CH] Switzerland ............... 2141/88

[51] Int. Cl.⁵ ......................................... C07D 277/20
[52] U.S. Cl. .................................. 514/318; 514/343; 514/357; 514/332; 546/193; 546/281; 546/330; 546/264
[58] Field of Search ............... 546/255, 256, 275, 281, 546/330, 193, 264; 514/332, 333, 340, 343, 357, 318

[56] References Cited

U.S. PATENT DOCUMENTS 2,697,727 12/1954 Kaiser et al. .................. 260/551
3,074,955 1/1963 Shapiro et al. ................ 260/295
4,098,791 7/1978 Hylton et al. ................. 260/293.87
4,647,570 3/1987 Shiokawa et al. .............. 514/341
4,678,795 7/1987 Shiokawa et al. .............. 514/341
4,680,294 7/1987 Shiokawa et al. .............. 514/256
4,707,478 11/1987 Studt et al. ................... 514/580

FOREIGN PATENT DOCUMENTS 0126558 11/1984 European Pat. Off. ........ 514/341
0235725 9/1987 European Pat. Off. ........ 546/275
1443913 11/1972 Fed. Rep. of Germany ..... 546/275
3148103 6/1983 Fed. Rep. of Germany ..... 548/343

OTHER PUBLICATIONS

*Journal of Medicinal Chemistry*, vol. 21, No. 8, (1978) pp. 773–781.

*Journal of Heterocyclic Chemistry*, vol. 23 (1986) pp. 401–408.
Chemical Abstract, vol. 85 (1976) 159372z.
*Journal of Praktische Chemie*, vol. 318 (1976) pp. 479–482.
Arch Pharm, 310, pp. 820–827 (1977).
Arch Pharm, 320, pp. 617–620 (1987).
*Journal of Praktische Chemie vol. 323 (1981) pp. 694–699.*
Arzneim—Forsch/Drug Res. 29(I) NR4 (1979).
Yuki Gosa Kagaku Kyokai, vol. 29, No. 1 (1971).
Chem. Ber. 101, 3185–3200 (1968).
Chem. Ber. 100, 2604–2615 (1967).
Chemical Abstract, vol. 90, 87289f.

*Primary Examiner*—C. Warren Ivy
*Assistant Examiner*—Zinna Nortinghton-Davis
*Attorney, Agent, or Firm*—Kevin T. Mansfield; Edward McC. Roberts

[57] ABSTRACT

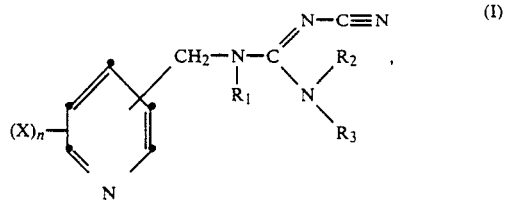

in which each of $R_1$ and $R_3$, independently of the other, is hydrogen or $C_1$-$C_4$alkyl; $R_2$ is hydrogen, $C_1$-$C_4$alkyl, benzyl or picolyl; or $R_2$ and $R_3$ are together a -$(CH_2)_4$- or -$(CH_2)_5$- radical; X is halogen; and n is an integer 0, 1, 2 or 3; and the salts of compounds of formula I; with the execption of N-picolyl-N'-cyanoguanidine and N-picolyl-N'-methyl-N''-cyanoguanidine. Also described are processes fot the preparation of these compounds, the corresponding starting materials and intermediates, and the use of the novel compounds in pest control, especially for controlling insects and representatives of the order Acarina, particularly insect pests in rice crops.

8 Claims, No Drawings

PYRIDYL SUBSTITUTED GUANIDINES USEFUL AS INSECTICIDES

The present invention relates to novel substituted N-pyridylmethyl-N'-cyanoguanidines and to their use in controlling pests.

The invention relates to novel compounds of formula I and tautomers thereof

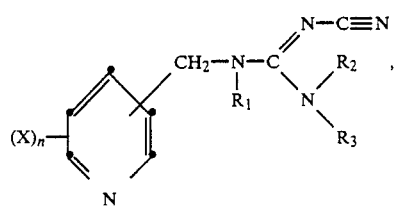

in which each of $R_1$ and $R_3$, independently of the other, is hydrogen or $C_1$–$C_4$alkyl; $R_2$ is hydrogen, $C_1$–$C_4$alkyl, benzyl or picolyl; or $R_2$ and $R_3$ are together a —(CH$_2$)$_4$— or —(CH$_2$)$_5$— radical; X is halogen; and n is an integer 0, 1, 2 or 3; and to the salts of compounds of formula I; with the exception of N-picolyl-N-methyl-N'-cyanoguanidine and N-picolyl-N'-methyl-N"-cyanoguanidine.

Of special interest are compounds of formula I in which each of $R_1$ and $R_3$, independently of the other, is hydrogen or $C_1$–$C_4$alkyl; $R_2$ is hydrogen, $C_1$–$C_4$alkyl, benzyl or picolyl; or $R_2$ and $R_3$ are together a —(CH$_2$)$_4$— or —(CH$_2$)$_5$— radical; X is halogen; and n is an integer 0, 1, 2 or 3.

Compounds of formula I according to the invention in which $R_1$ and $R_3$ are hydrogen or methyl; $R_2$ is hydrogen, $C_1$–$C_4$alkyl or benzyl; or $R_2$ and $R_3$ are together a —(CH$_2$)$_5$—radical; X is chlorine and n is an integer 0, 1 or 2, are preferred.

Attention is drawn especially to compounds of formula I in which n is 0. Also preferred are those compounds of formula I according to the invention in which $R_1$ is hydrogen or methyl; $R_2$ is hydrogen or $C_1$–$C_4$alkyl; $R_3$ is hydrogen, methyl or ethyl; and n is the integer 0.

Owing to their biological activity, those compounds of formula I according to the invention in which the pyridyl radical is pyrid-3-yl or pyrid-4-yl are of particular interest.

There is to be understood by "alkyl", on its own or as a component of another substituent, a straight-chained or branched alkyl group and, depending on the number of carbon atoms indicated within the scope of the present invention, for example one of the following groups: methyl, ethyl, propyl, butyl, and the isomers thereof, such as isopropyl, cyclopropyl, isobutyl, tert.-butyl and sec.-butyl.

The term "halogen" within the scope of the present invention is to be understood as meaning fluorine, chlorine and bromine, preferably fluorine and chlorine.

The present invention includes under compounds of formula I in which $R_2$ or $R_3$ is hydrogen also tautomers thereof:

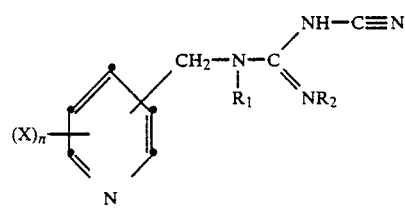

and

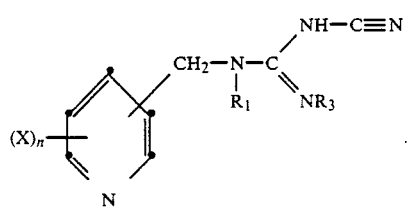

The present invention also relates to salts, especially non-toxic salts physiologically tolerated by plants, of compounds of formula I. The following, for example, are suitable salts of this kind with organic and inorganic acids: chlorides, bromides, iodides, sulfates, hydrogen sulfates, chlorates, perchlorates, thiocyanates, nitrates, phosphates, hydrogen phosphates, tetrafluoroborates, formates, acetates, trichloroacetates, trifluoroacetates, phenylsulfonates, oxalates, malonates, succinates, malates, tartrates and citrates.

The compounds of formula I and salts thereof can be prepared by a) reacting a compound of formula II

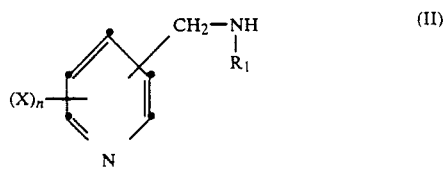

with a compound of formula III

and with a compound of formula IV

or b) for the preparation of a compound of formula I in which $R_2$ and $R_3$ are hydrogen, reacting a compound of formula II with dicyanimide; whereby in the above formulae II to IV each of $R_1$ and $R_3$, independently of the other, is hydrogen or $C_1$–$C_4$alkyl; $R_2$ is hydrogen, $C_1$–$C_4$alkyl, benzyl or picolyl; or $R_2$ and $R_3$ are together a —(CH$_2$)$_4$— or —(CH$_2$)$_5$— radical; X is halogen; and n is an integer 0, 1, 2 or 3; and $Y_1$ and $Y_2$ are removable leaving groups;

and, if desired, a compound of formula I obtained according to a) or b) is converted in a manner known per se into one of its salts.

The above process variants a) and b) can also be carried out by first of all reacting a compound of formula II with a compound of formula III to form an isolatable intermediate of formula V

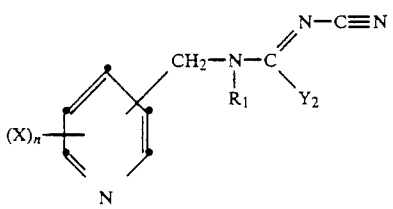

and then reacting the resulting intermediate of formula V with a compound of formula IV, $R_1$, $R_2$, $R_3$, X, n, $Y_1$ and $Y_2$ having the meanings given above in a) and b).

Process variants a) and b) can also be carried out by first of all reacting a compound of formula III with a compound of formula IV to form an intermediate of formula VI

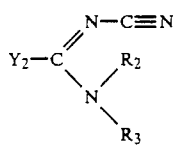

and then reacting the resulting intermediate of formula VI with a compound of formula II, $R_1$, $R_2$, $R_3$, X, n, $Y_1$ and $Y_2$ having the meanings given above.

The compounds of formula V and VI are novel and as such also form part of the present invention.

Within the scope of the process variants described above, suitable removable leaving groups in compounds of formulae III and VI are, for example, as follows:

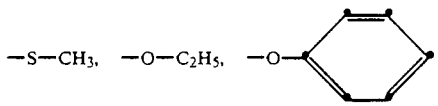

The above process variants resulting in the compounds of formula I according to the invention are preferably carried out in a solvent. Suitable solvents are, for example, aromatic hydrocarbons, such as benzene, toluene and xylene; ketones, such as acetone, cyclohexanone and methyl ethyl ketone; ethers, such as tetrahydrofuran, dioxan and diethyl ether; halogenated hydrocarbons, such as chloroform, carbon tetrachloride and chlorobenzene; alcohols, such as ethanol and propanol; esters of aliphatic acids, such as ethyl acetate; aliphatic amides, such as dimethylformamide and dimethylacetamide; dimethyl sulfoxide, acetonitrile and other solvents that do not impair the reaction. These solvents can also be used in the form of mixtures. The reaction temperature may be in a wide range of from −10° to +150° C. A temperature range of approximately from 20° to 80° C. is preferred.

The above described procedures for preparing compounds of formula I are known per se and are set forth in principle in EP Patent Applications Nos. 2930 and 161 841, U.S. Pat. No. 2,455,807 and DE-OS No. 340 980.

The starting compounds of formulae II, III and IV are known or, if novel, can be obtained analogously to known methods. For example, N-cyanothioiminocarbonates of formula III, and the preparation thereof, are known from Chem. Ber. 100, 2604-15 (1967); J. Hetero. Chem. 19, 1205-6 (1982), Arch. Pharm. 318, 888 (1985) and JP Patent Application SHO 61-76044. Picolylamine compounds of formulae II are known or can be obtained analogously to known processes [cf. Tetrahedron Letters 26, 5863 (1985)]. Some of the N-pyridylmethyl-N'-cyano-, iso- and isothio-urea compounds of the formula V type in which $R_1$=H or $R_2$=H and the preparation thereof are known [cf. JP Patent Application SHO 61-76044; Arch. Pharm. 318, 888 (1985)]; the compounds of formula V in which $R_1$ or $R_2$ and/or $R_3$ are $C_1$-$C_4$alkyl can be obtained in a corresponding manner, for example by reacting an amine of formula II with an N-cyanoiminocarbonate of formula III.

Certain N-picolyl-N-methyl-N'-cyanoguanidines, their preparation and their use as intermediates for the synthesis of pharmaceuticals have already been described in U.S. Pat. No. 3,147,271. The preparation of pharmaceutically active N-picolyl-N'-methyl-N''-cyanoguanidines is also mentioned in C.A. Vol. 90 (1979) 90:87289 f.

It has now surprisingly been found that the novel guanidine compounds of formula I according to the invention have excellent insecticidal properties while being well tolerated by plants and having low toxicity to warm-blooded animals. They are suitable especially for controlling pests that attack plants and animals.

The compounds of formula I are especially suitable for controlling insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera and representatives of the order Acarina.

The good pesticidal activity of the compounds of the invention corresponds to a mortality rate of at least 50-60% of the pests mentioned.

Using the compounds of formula I of the invention it is possible especially for plant-damaging insects, especially plant-damaging insects in crops of ornamental and useful plants, especially cotton crops, vegetable crops, rice crops and fruit crops, to be controlled. In this connection, attention is drawn to the fact that the said compounds are distinguished by a strongly pronounced systemic action, but especially by contact action, against sucking insects, especially against insects of the Aphididae family (such as, for example, Aphis fabae, Aphis craccivora and Myzus persicae), that can be controlled by conventional compositions only with difficulty.

The compounds of formula I are furthermore distinguished by a good activity against larval insect stages and against nymphs, especially of feeding insect pests. In particular, the compounds of formula I can be used with excellent success against plant-damaging cicadas, especially in rice crops. In this connection attention is drawn to the low toxicity to fish of the compounds of the invention.

The compounds are also suitable for controlling ectoparasites, for example Lucilia sericata, and ticks on domestic animals and productive livestock, for example by treating the animals, livestock buildings and pastures.

The activity of the compounds of the invention and of compositions containing them can be broadened substantially and adapted to the given circumstances by adding other insecticides and/or acaricides. Possible additives are, for example, representatives of the following classes of active substance: organic phosphorus compounds, nitrophenols and derivatives, formamidines, ureas, carbamates, pyrethroids, chlorinated hydrocarbons and Bacillus thuringiensis preparations.

The compounds of formula I are used in unmodified form or, preferably, together with the adjuvants conventionally employed in the art of formulation, and are therefore formulated in known manner e.g. into emulsifiable concentrates, directly sprayable or dilutable solutions, dilute emulsions, wettable powders, soluble powders, dusts, granulates, and also encapsulations in e.g. polymer substances. As with the compositions, the methods of application, such as spraying, atomising, dusting, scattering or pouring, are chosen in accordance with the intended objectives and the prevailing circumstances.

The formulations, i.e. the compositions, preparations or mixtures containing the active ingredient or combinations of these active ingredients with other insecticides or acaricides and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane, paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers, such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of granulated materials of inorganic or organic nature can be used, e.g. especially dolomite or pulverised plant residues.

Depending on the nature of the active ingredient of formula I to be formulated, or of the combination of these active ingredients with other insecticides or acaricides, suitable surface-active compounds are nonionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tall oil. Other suitable surfactants that may be mentioned are fatty acid methyltaurin salts and modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing approximately from 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are especially polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenol-polyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are especially quaternary ammonium salts that contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customary in the art of formulation are described inter alia in the following publications:

"Mc Cutcheon's Detergents and Emulsifiers Annual" MC Publishing Corp., Ridgewood, N.J., 1979;

Dr. Helmut Stache "Tensid Taschenbuch", Carl Hanser Verlag, Munich/Vienna 1981.

The pesticidal formulations usually contain—based on weight—0.1 to 99%, especially 0.1 to 95%, of an active ingredient of formula I or combinations thereof with other insecticides or acaricides, 1 to 99.9% of a solid or liquid adjuvant, and 0 to 25%, especially 0.1 to 20%, of a surfactant. Whereas commercial products will preferably be formulated as concentrates, the end user will normally employ dilute formulations containing substantially lower concentrations of active ingredient, for example from 0.1 to 1000 ppm.

The compositions may also contain further adjuvants such as stabilisers, antifoams, viscosity regulators, binders, tackifiers as well as fertilisers or other active ingredients for obtaining special effects.

EXAMPLE 1

Preparation of N-pyrid-3-ylmethyl-N'-ethyl-N''-cyanoguanidine 6.2 g of N-pyrid-3-ylmethyl-N'-cyano-S -methylisothiourea are stirred together with 30 ml of ethylamine (70% in water) for one hour at 60° C. and then heated for 30 minutes at 80° C. The product that crystallises out when the mixture is cooled is washed with cold water and corresponds to the title compound of formula

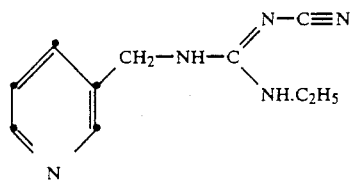

having a melting point of 177°-179° C. (compound No. 1).

EXAMPLE 2

Preparation of N-pyrid-3-ylmethyl-N'-methyl-N'-n-butyl-N''-cyanoguanidine 7.31 g of dimethyl-N-cyanothioiminocarbonate, 4.79 g of n-butylmethylamine (in 20 ml of acetonitrile) and 20 mg of dimethylaminopyridine are together maintained at 70° C. for one hour. When the solvent has been removed, N,S-dimethyl-N-n-butyl-N'-cyanoisothiourea is obtained in the form of an oil. This oil is maintained at reflux for 30 minutes together with 6.41 g of 3-picolylamine and 5.5 g of 1,4-diazabicyclo[2.2.2]octane (in 30 ml of toluene). The solvents are then removed, the residue is taken up in dichloromethane and the solution is washed in succession, in each case twice, with $H_2O$, 2N NaOH solution and saturated sodium chloride solution. The dichloromethane solution is dried over $Na_2SO_4$ and concentrated. The crude product remaining as residue is chromatographed on silica gel using dichloromethane/methanol (0-10%) and recrystallised from acetone/ether, yielding the title compound of formula

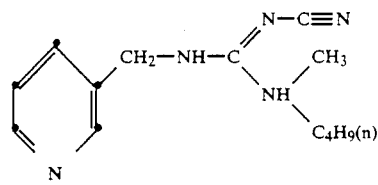

having a melting point of 65°-69° C. (compound No. 2).

The following compounds of formula I are prepared in the manner indicated above:

| Compound No. | pyridyl position | $R_1$ | $R_2$ | $R_3$ | n | X | physical data |
|---|---|---|---|---|---|---|---|
| 3 | 3- | H | H | H | O | — | mp = 72-73° C. |
| 4 | 3- | —$CH_3$ | —$C_4H_9(n)$ | H | O | — | $n_D^{22}$ = 1.5595 |
| 5 | 3- | H | —$C_4H_9(n)$ | H | O | — | mp = 87-90° C. |
| 6 | 3- | H | —$CH_2$—⟨phenyl⟩ | H | O | — | mp = 178-180° C. |
| 7 | 3- | H | ─(CH₂)₄─ | | O | — | mp = 151-153° C. |
| 8 | 4- | H | —$CH_2CH_3$ | H | O | — | mp = 150-152° C. |
| 9 | 4- | H | —$C_4H_9(n)$ | H | O | — | mp = 126-129° C. |
| 10 | 4- | H | ─(CH₂)₃─ | | O | — | mp = 160-163° |
| 11 | 4- | H | —$CH_2$—⟨phenyl⟩ | H | O | — | mp = 153-156° C. |
| 12 | 3- | —$CH_3$ | —$C_3H_7(i)$ | H | O | — | viscous oil |
| 13 | 3- | H | —$CH_3$ | —$CH_3$ | O | — | mp = 70.5-75.5° C. |
| 14 | 3- | H | —$C_3H_7(i)$ | H | O | — | mp = 164-165.5° C. |
| 15 | 3- | H | —$C_2H_5$ | —$C_2H_5$ | O | — | viscous oil |
| 16 | 3- | H | —$C_4H_9(i)$ | H | O | — | mp = 125.5-127° C. |

-continued

| Compound No. | pyridyl position | R$_1$ | R$_2$ | R$_3$ | n | X | physical data |
|---|---|---|---|---|---|---|---|
| 17 | 3- | H | —CH$_2$—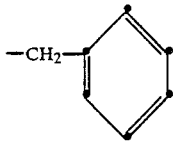 | —CH$_3$ | O | — | mp = 123–126° C. |
| 18 | 3- | —CH$_3$ | —C$_4$H$_9$(i) | H | O | — | viscous oil |
| 19 | 4- | H | —CH$_3$ | —CH$_3$ | O | — | mp = 121–122.5° C. |
| 20 | 4- | H | H | —C$_3$H$_7$(i) | O | — | mp = 159–161° C. |
| 21 | 4- | H | —CH$_3$ | —C$_4$H$_9$(n) | O | — | mp = 130.5–137.5° C. |
| 22 | 3- | —CH$_3$ | —CH$_3$ | —CH$_3$ | O | — | n$_D^{25}$ = 1.5772 |
| 23A | 4- | —C$_3$H$_7$(n) | H | —CH$_3$ | O | — | resin (tautomer A) |
| 23B | 4- | —C$_3$H$_7$(n) | H | —CH$_3$ | O | — | resin (tautomer B) |
| 24 | 3- | —C$_4$H$_9$(n) | H | —CH$_3$ | O | — | resin |
| 25A | 4- | —C$_3$H$_7$(n) | H | —C$_3$H$_7$(n) | O | — | resin (tautomer A) |
| 25B | 4- | —C$_3$H$_7$(n) | H | —C$_3$H$_7$(n) | O | — | resin (tautomer B) |
| 26 | 2- | H | H | —C$_3$H$_7$(i) | O | — | mp = 125.5–127° C. |
| 27 | 2- | H | —CH$_3$ | —C$_4$H$_9$(n) | O | — | n$_D^{24}$ = 1.559 |

It is also possible to prepare the following compounds of formula I analogously to the procedures described above:

| pyridyl position* | R$_1$ | R$_2$ | R$_3$ |
|---|---|---|---|
| 3- | —C$_2$H$_5$ | —C$_3$H$_7$(i) | H |
| 4- | H | —C$_3$H$_7$(i) | H |
| 3- | H | —C$_4$H$_9$(s) | H |
| 4- | H | —C$_2$H$_5$ | —C$_2$H$_5$ |
| 3- | H | —CH$_3$ | —C$_2$H$_5$ |
| 3- | H | —CH$_3$ | —C$_4$H$_9$(n) |
| 3- | —CH$_3$ | —CH$_2$—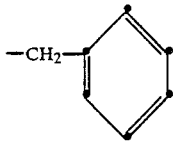 | H |
| 3- | 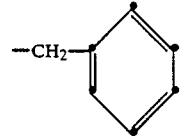 | —CH$_3$ | H |
| 2- | H | H | H |
| 4- | H | H | H |
| 3- | 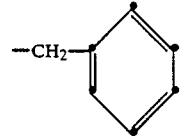 | —C$_3$H$_7$(i) | H |
| 3- | —CH$_3$ | 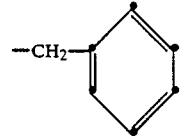 | H |

*n = 0

EXAMPLE 3

Formulations for active ingredients of formula I according to Examples 1 to 2, or for combinations of these active ingredients with other insecticides or acaricides (%=percent by weight)

| 1. Wettable powders | a) | b) | c) |
|---|---|---|---|
| active ingredient or active ingredient combination | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient or the active ingredient combination is mixed with the adjuvants and the mixture is thoroughly ground in a suitable mill, affording wettable powders which can be diluted with water to give suspensions of the desired concentration.

| 2. Emulsifiable concentrate | |
|---|---|
| active ingredient or active ingredient combination | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 3. Dusts | a) | b) |
|---|---|---|
| active ingredient or active ingredient combination | 5% | 8% |
| talcum | 95% | — |

-continued

| 3. Dusts | a) | b) |
|---|---|---|
| kaolin | — | 92% |

Ready-for-use dusts are obtained by mixing the active ingredient with the carrier and grinding the mixture in a suitable mill.

| 4. Extruder granulate | |
|---|---|
| active ingredient or active ingredient combination | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded, granulated and then dried in a stream of air.

| 5. Coated granulate | |
|---|---|
| active ingredient or active ingredient combination | 3% |
| polyethylene glycol (MW 200) | 3% |
| kaolin | 94% |

The finely ground active ingredient or the active ingredient combination is uniformly applied, in a mixer, to the kaolin moistened with polyethylene glycol. Non-dusty coated granulates are obtained in this manner.

| 6. Suspension concentrate | |
|---|---|
| active ingredient or active ingredient combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or the active ingredient combination is intimately mixed with the adjuvants, giving a suspension concentrate from which suspensions of any desired concentration can be obtained by dilution with water.

EXAMPLE 4

Action against Lucilia sericata 1 ml of an aqueous formulation containing 0.1% active ingredient is added at 50° C. to 9 ml of a culture medium. Approximately 30 newly hatched Lucilia sericata larvae are then added to the culture medium. The insecticidal action is determined after 48 and 96 hours by ascertaining the mortality rate.

Compounds of formula I according to Examples 1 to 2 exhibit a good activity (mortality rate) against Lucilia sericata in this test.

EXAMPLE 5

Action against Aedes aegypti

A 0.1% solution of the active ingredient in acetone is pipetted onto the surface of 150 ml water in a container in an amount sufficient to produce a concentration of 400 ppm. When the acetone has evaporated the container is charged with from 30 to 40 2 day-old Aedes larvae. The percentage mortality (number of larvae unable to swim) is assessed after 2 and 7 days.

Compounds of formula I according to Examples 1 to 2 exhibit a good activity (mortality rate) in this test.

EXAMPLE 6

Insecticidal contact action: Aphis craccivora

Before the beginning of the test, plants (Vicia faba) grown in pots are each populated with about 200 specimens of the species Aphis craccivora. 24 hours later, the plants treated in this manner are sprayed to drip point with an aqueous formulation containing 400 ppm of the test compound. Two plants are used per test compound, and an evaluation of the mortality rate achieved is carried out after a further 24 hours.

Compounds of formula I according to Examples 1 to 2 exhibit a good activity (mortality rate) in this test.

EXAMPLE 7

Systemic insecticidal action: Aphis craccivora

Rooted bean plants are planted in pots containing 600 ccm of soil. 50 ml of a formulation of the test compound (obtained from a 25% wettable powder), in a concentration of 400 ppm, is then poured directly onto the soil in each pot.

After 24 hours aphids of the species Aphis craccivora are placed on the parts of the plant above soil level and a plastics cylinder is slipped over the plants in order to protect the aphids from any possible contact action or gas action of the test substance.

An evaluation of the mortality rate achieved is made 48 and 72 hours after the beginning of the test. Two plants, each in a separate pot, are used per test substance. The test is carried out at 25° C. and 70% relative humidity.

The compounds of formula I according to Examples 1 to 2 exhibit a good activity in this test.

EXAMPLE 8

Insecticidal contact action: Myzus persicae

Pea seedlings approximately 4 cm high that have been grown in water are each populated before the beginning of the test with about 200 specimens of the species Myzus persicae. The plants treated in this manner are 24 hours later sprayed to drip point with an aqueous suspension containing 400 ppm of the test compound. Two plants are used per compound and concentration. An evaluation of the mortality rate achieved is carried out 48 hours after application. The test is carried out at from 20° to 22° C. and 60% relative humidity.

The compounds of formula I according to Examples 1 to 2 exhibit a good activity in this test.

EXAMPLE 9

Systemic insecticidal action: Myzus persicae

Rooted cabbage plants at the 4- to 5-leaf stage are transplanted into pots containing 60 ccm of soil. 50 ml of an aqueous formulation of test compound of formula I (obtained from a 25% wettable powder), in each case in a concentration of 400 ppm, are then poured directly onto the soil.

After 24 hours aphids of the species Myzus persicae are placed on the parts of the treated plants that are above soil level and plastics cylinders are slipped over the plants in order to protect the aphids from any possible contact action or gas action of the test substance.

An evaluation of the percentage mortality achieved is made 48 hours after the beginning of the test. Two plants, each in a separate pot, are used per test substance. The test is carried out at approximately 25° C. and 60% relative humidity.

The compounds of formula I according to Examples 1 to 2 exhibit a good activity in this test.

EXAMPLE 10

Insecticidal leaf penetration action: Aphis craccivora

A suitably small sprig of Vicia faba heavily infested with aphids of the species Aphis craccivora is placed into each of a number of plastics beakers approximately 8 cm in height (diameter approximately 6 cm). Each beaker is covered with a plastics lid that has a hole of 2 cm diameter punched in the middle. A leaf of a Vicia faba plant is placed on the hole in the lid without this leaf being separated from the potted plant. The leaf is then fixed by a second perforated lid on the beaker over the hole in the first lid. From the underside, that is to say through the hole in the first lid, the aphids in the beaker then infest the overlying leaf of the feed plant. An aqueous preparation of the test compound is uniformly applied in a concentration of 400 ppm to the upper side of the leaf using a brush. An examination is made to determine whether the test substance applied to the upper side of the leaf of the feed plant has diffused through the leaf to the underside thereof in an amount that is sufficient to kill the aphids sucking there.

The test is carried out at approximately 20° C. and 60% relative humidity. The evaluation for percentage mortality is carried out 48 hours after application of the active ingredient.

Compounds of formula I according to Examples 1 to 2 exhibit a good activity in this test.

EXAMPLE 11

Insecticidal action (systemic-water): Aphis craccivora

Pea seedlings that have been infested with aphids 24 hours before the beginning of the test are placed in 20 ml of an aqueous mixture containing 400 ppm of the test compound. The aqueous mixture is prepared from an emulsifiable concentrate or a wettable powder formulation of the active ingredient in question and is contained in a vessel sealed with a plastics lid having holes. The roots of the infested pea plants are each pushed into the mixture through a hole in the plastics lid. The hole is then sealed with cotton wool in order to fix the plant in position and prevent any possible influence from the gaseous phase of the mixture. The test is carried out at 20° C. and 60% relative humidity. After 2 days the number of test insects no longer able to suck is evaluated by comparison with untreated controls. By this means it is possible to determine whether the active ingredient taken up through the roots kills the aphids on the upper parts of the plants.

Compounds of formula I according to Examples 1 to 2 exhibit a good systemic action against insects of the species Aphis craccivora in this test.

EXAMPLE 12

Stomach toxicant action and contact action on Laodelphax striatellus and Nilaparvata lugens (nymphs)

The test is carried out on growing plants. For this purpose in each case 4 rice plants (thickness of the stem 8 mm) approximately 20 cm in height are planted into pots (8 cm in diameter).

The plants are sprayed on a rotarytable with 100 ml of a solution in acetone containing 400 ppm of the active ingredient in question. When the spray coating has dried, each plant is populated with 20 nymphs of the test insects in the third stage. To prevent the cicadas from escaping, a glass cylinder open at both ends is slipped over each of the populated plants and this cylinder is closed with a gauze lid. The nymphs are kept on the treated plant over a period of 10 days until they have reached the next stage of development. An evaluation of the percentage mortality is made 1, 4 and 8 days after the treatment.

Compounds of formula I according to Examples 1 to 2 exhibit a good activity against Nilaparvata lugens in this test.

EXAMPLE 13

Systemic action on Nilaparvata lugens

Approximately 10 day-old rice plants (approximately 10 cm high) are each placed in a plastics beaker containing 20 ml of an aqueous emulsion formulation of the test compound in a concentration of 400 ppm that is closed with a plastics lid having holes. The roots of the rice plants are in each case pushed through a hole in the plastics lid into the aqueous test formulation. The hole is then sealed with cotton wool in order to fix the plant in position and prevent any possible inflence from the gaseous phase of the test formulation. The rice plant is then populated with 20 nymphs of Nilaparvata lugens in the N 2 to N 3 stage and covered with a plastics cylinder. The test is carried out at 20° C. and 60% relative humidity with an light exposure period of 16 hours. After 5 days the number of dead test insects is evaluated by comparison with untreated controls. By this means it is possible to determine whether the active ingredient taken up through the roots kills the test insects on the upper parts of the plants.

Compounds of formula I according to Examples 1 to 2 exhibit a good activity (mortality rate) against Nilaparvata lugens in this test.

EXAMPLE 14

Insecticidal stomach toxicant action and contact action

Potted cotton plants approximately 25 cm high are sprayed with aqueous emulsions containing the active ingredient in a concentration of 800 ppm.

When the spray coating has dried the cotton plants are populated with Spodoptera littoralis and Heliothis virescens larvae in the first larval stage. The test is carried out at 24° C. and approximately 60% relative humidity. After 120 hours the percentage mortality of the test insects is ascertained by comparison with untreated controls.

Compounds of formula I according to Examples 1 to 2 exhibit a good activity (mortality rate) in this test.

EXAMPLE 15

Action against Nephotettix cincticeps (nymphs)

The test is carried out on growing plants. For this purpose approximately 20 day-old rice plants about 15 cm in height are planted into pots (diameter 5.5 cm).

The plants are each sprayed on a turntable with 100 ml of a solution in acetone containing 400 ppm of the test compound. After the spray coating has dried, each plant is populated with about 20 nymphs of the test insects in the second or third stage. In order to prevent the cicadas from escaping, a plexiglass cylinder is slipped over each of the populated plants and closed with a gauze lid. The nymphs are kept for 5 days on the treated plants, which have to be watered at least once. The test is carried out at a temperature of approximately 23° C. at 55% relative humidity and with an light exposure period of 16 hours.

Compounds of formula I according to Examples 1 to 2 exhibit a good activity in this test.

What is claimed is:

1. A compound of formula I and tautomers thereof

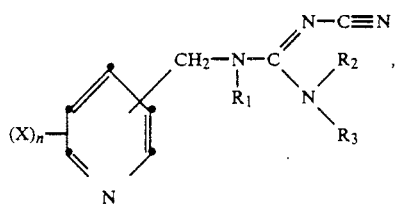

in which each of $R_1$ and $R_3$, independently of the other, is hydrogen or $C_1$–$C_4$alkyl; $R_2$ is hydrogen, $C_1$–$C_4$alkyl, benzyl or picolyl; or $R_2$ and $R_3$ are together a —(CH$_2$)$_4$— or —(CH$_2$)$_5$— radical; X is halogen; and n is an integer 1, 2 or 3; or a salt thereof 2. A compound of formula I according to claim 1, wherein $R_1$ and $R_3$ are hydrogen or methyl; $R_2$ is hydrogen, $C_1$–$C_4$alkyl or benzyl; or $R_2$ and $R_3$ are together a —(CH$_2$)$_5$—radical; X is chlorine and n is an integer 1 or 2.

3. A compound of formula I according to claim 1, wherein the pyridyl radical is a pyrid-3-yl or pyrid-4-yl radical.

4. A compound of formula V

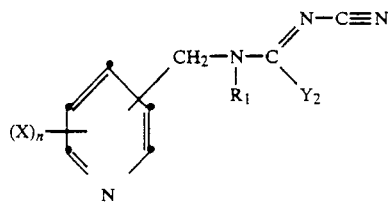

wherein $R_1$, X and n are as defined in claim 1 and $Y_2$ is —S—CH$_3$—O—C$_2$H$_5$ or —O—C$_6$H$_5$.

5. A composition for controlling insect pests and pests of the order Acarina containing as active component at least one compound of formula I according to claim 1 and a carrier therefor.

6. A compound of formula I according to claim 1, wherein $R_1$ is hydrogen or methyl; $R_2$ is hydrogen or $C_1$–$C_4$alkyl; $R_3$ is hydrogen, methyl or ethyl; and n is the integer 1, 2 or 3.

7. A method of controlling insects and representatives of the order Acarina which comprises bringing into contact or treating said pests, or various stages of development thereof or the locus thereof, with a pesticidally effective amount of a compound of formula I and tautomers thereof

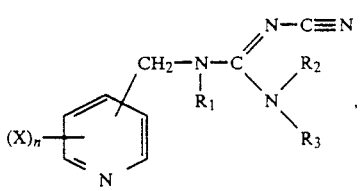

in which each of $R_1$ and $R_3$, independently of the other, is hydrogen or $C_1$–$C_4$alkyl; $R_2$ is hydrogen, $C_1$–$C_4$alkyl, benzyl or picolyl; or $R_2$ and $R_3$ are together a —(CH$_2$)$_4$— or —(CH$_2$)$_5$—radical; X is halogen; and n is an integer 0, 1, 2 or 3; or a salt of a compound of formula I; with the exception of N-picolyl-N-methyl-N'-cyanoguanidine and N-picolyl-N'-methyl-N''-cyanoguanidine; or with a composition containing a pesticidally effective amount of said compound together with a carrier or other adjuvant.

8. A method according to claim 7 for controlling feeding insect pests in rice crops.

* * * * *